US00PP31111P3

(12) United States Plant Patent
Karniel

(10) Patent No.: US PP31,111 P3
(45) Date of Patent: Nov. 26, 2019

(54) SEEDLESS TABLE GRAPE (GRAPEVINE) NAMED 'ARRATWENTYFOUR'

(50) Latin Name: *Vitis vinifera*
Varietal Denomination: ARRATWENTYFOUR

(71) Applicant: AGRICULTURAL RESEARCH AND DEVELOPMENT LIMITED LIABILITY COMPANY, Bakersfield, CA (US)

(72) Inventor: Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 0 days.

(21) Appl. No.: 15/732,301

(22) Filed: Oct. 20, 2017

(65) Prior Publication Data

US 2019/0124810 P1 Apr. 25, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812; A01H 5/08; A01H 5/00; A01H 5/02; A01H 6/88; A01H 5/0806
See application file for complete search history.

*Primary Examiner* — June Hwu
(74) *Attorney, Agent, or Firm* — Lewis Roca Rothgerber Christie LLP

(57) ABSTRACT

A new distinct variety of grapevine named ARRATWENTYFOUR abundantly forms attractive moderately firm seedless berries with an attractive purple-black skin coloration; in semi-tight clusters which display a naturally sweet flavor. The fruit commonly is ready for harvesting during June in San Joaquin Valley of Central California, U.S.A, and displays good eating qualities as a table grape. The fruit meatiness and firmness renders the fruit amenable for handling, shipping, and storage.

1 Drawing Sheet

Classification: The present invention relates to a new *Vitis vinifera* Grapevine.

Variety denomination: The new Grapevine has a varietal denomination 'ARRATWENTYFOUR'.

BACKGROUND OF THE INVENTION

A breeding program was initiated during the late 90's near Bakersfield in San Joaquin Valley of Central California. In 2004, during this breeding program, a new variety of *Vitis vinifera* was created by deliberate cross breeding of two parent plants by emasculation of the pollen bearing organ of the female and introducing pollen from another male origin. The female parent of the new variety was GSB5, a medium-sized black almost seedless grape variety with a fleshy texture and a natural flavor (non-patented in the United States). The male parent (i.e. the pollen parent) of the new variety was GRW3, a vigorous black variety with a crisp texture and a natural flavor (non-patented in the United States).

TABLE 1

Comparison of ARRATWENTYFOUR with its parents and the closest related variety:

| | ARRA-TWENTY-FOUR | GSB5 | GRW3 | Summer Royal (Comparison Variety) |
|---|---|---|---|---|
| Berry attachment | Medium | Good | Very Good | Good |

TABLE 1-continued

Comparison of ARRATWENTYFOUR with its parents and the closest related variety:

| | ARRA-TWENTY-FOUR | GSB5 | GRW3 | Summer Royal (Comparison Variety) |
|---|---|---|---|---|
| Berry size | 20-22 | 20-22 | 18-22 | 18-20 |
| Bunches per vine | 32 | 32-36 | 32 | 42 |
| Bunch Density | Semi tight | Tight | Medium | Slightly loose |

The parentage of the new variety can be summarized as follows:

GSB5 X GRW3

An artificial pollination was created, and the result was an embryo which possessed unique genetic qualities. The rudiments resulting from the above pollination were embryo rescued.

In 2006 the plant was transplanted to Bakersfield in San Joaquin Valley of Central California.

It was found that the new grapevine of the present invention possesses the following combination of characteristics:

(a) Forms attractive moderately firm seedless berries with a purple-black skin coloration; in semi-tight clusters which display a naturally sweet flavor, (b) Commonly bears fruit during the month of June in the San Joaquin Valley of Central California, U.S.A., and (c) Bears fruit that is moderately firm and is amenable for storage, handling, and shipping.

The new variety during observation to date has displayed no visible disease, and has displayed an ability to well resist cold, drought, heat; but sensitive to direct exposure to sun and wind. The fruit of the new variety has been found to display qualities suitable for handling and shipping combined with desirable dessert eating qualities.

The new variety of the present invention has been found to undergo asexual propagation beginning in 2006 near Bakersfield in the San Joaquin Valley of Central California, U.S.A. by bud grafting on mature Thompson rootstock (non-patented in the United States). Such asexual propagation was conducted successively from 2006 until 2007 for a total of two growing seasons, and has shown that the characteristics of the new variety are strictly transmissible from one generation to another. Accordingly, the new variety undergoes asexual propagation in a true to type manner.

SUMMARY OF THE INVENTION

The new variety ARRATWENTYFOUR is a purple-black seedless table grape with medium production, e.g., about 32 bunches per vine, and an average of about one to two bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical specimens of vegetative growth of six year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATWENTYFOUR'

DETAILED BOTANICAL DESCRIPTION

The chart used in the identification of colors is The R.H.S. Colour Chart of The ROYAL HORTICULTURAL SOCIETY, 3rd edition, 1995. The description is based on the observation of plants growing on 'Thompson Seedless' rootstock outdoors near San Joaquin Valley of Central California, U.S.A.

Vine:

*Vigor.*—Vigorous upright shoots.

*Productive capacity.*—Bearing at a natural, average capacity. Spur pruning.

*Trunk.*—Strong and developed. Diameter ranges from 2"-2⅜" (measured 9.2" from ground). Rough with a fibrous, shaggy exterior. Light maple brown coloring. RHS: grayed orange 177-B.

Time of bud burst:

*Early.*—February 20$^{th}$ in Bakersfield, Calif.

Young shoot:

*Openness of tip.*—Fully open.

*Prostrate hairs on tip.*—Absent or very sparse.

*Anthocyanin coloration of prostrate hairs on tip.*—Absent/very weak (yellow-green 144A).

*Erect hairs on tip.*—Absent or very sparse.

Young leaf:

*Color of upper side of blade.*—Yellow-green 152A.

*Prostrate hairs between main veins on lower side of blade.*—Absent or very sparse.

*Erect hairs on main veins on lower side of blade.*—Absent or very sparse.

Shoot:

*Attitude (before tying).*—Semi-erect.

*Color of dorsal side of internodes.*—Green (yellow green 144 C).

*Color of ventral side of internodes.*—Green (yellow green 144 C).

*Color of dorsal side of nodes.*—Green (yellow green 146 C).

*Color of ventral side of nodes.*—Green (yellow green 146 C).

*Erect hairs on internodes.*—Absent or very sparse.

*Average length of tendrils.*—7.55 inches.

*Color of tendrils.*—Yellow green 145A.

*Number of tendrils.*—2.

Flower:

*Sexual organs.*—Reflexed stamens and fully developed gynoecium.

*Length of first inflorescence.*—7.35 inches.

*Position of first flowering and fruiting node.*—4th node from base of branch.

*Number of inflorescence per flowering shoot.*—2.

*Time of bloom.*—First bloom April 23rd in Bakersfield, Calif.

*Date of full bloom.*—April 27th in Bakersfield, Calif.

Reproductive organs:

*Organ described.*—Stamen.

*Color.*—Yellow green 144B.

*Size.*—0.0147".

Mature leaf:

*Size of blade.*—Medium 7.5"×8".

*Shape of blade.*—Wedge-shaped.

*Blistering of upper side of blade.*—Medium.

*Number of lobes.*—Five.

*Depth of upper lateral sinuses.*—Medium.

*Arrangement of lobes of upper lateral sinuses (only varieties with lobed leaves).*—Slightly overlapped.

*Arrangement of lobes of petiole sinus.*—Wide open.

*Length of teeth.*—Medium.

*Ratio length width of teeth.*—Medium.

*Shape of teeth.*—Both sides straight.

*Proportion of main veins on upper side of blade with anthocyanin coloration.*—High (yellow green 152B).

*Prostrate hairs between main veins on lower side of blade.*—Sparse.

*Erect hairs on main veins on lower side of blade.*—Sparse.

*Length of petiole compared to length of middle vein.*—Much shorter.

*Top side color.*—Green 137 B.

*Bottom side color.*—Yellow green 146 D.

*Texture.*—Slightly rough.

*Vein color.*—Yellow green 145 C.

*Petiole length.*—4.5".

*Petiole color.*—Yellow green 152A.

*Leaf base.*—Cordate.

*Leaf margin.*—Serrate.

*Leaf apex.*—Apiculate.

Time of beginning of ripening:

*Mid.*—June 1st in Bakersfield, Calif.

Bunch:

*Diameter of bunch in inches.*—5".

*Length of bunch in inches.*—9".

*Density.*—Medium.

*Peduncle color.*—Yellow green 114-C.

*Length of peduncle of primary bunch.*—Short 2.3".

*Diameter of peduncle of primary bunch.*—0.327".

*Average bunch weight.*—1.8 lbs.

Berry:

*Size.*—Large.

*Length.*—0.9".

*Weight.*—0.21 oz.

*Diameter.*—0.8".

*Shape.*—Broad ellipsoid.

*Color of skin* (*without bloom*).—Dark red violet (black 202A).

*Ease of detachment from pedicel.*—Moderately easy.

*Thickness of skin.*—Thin.

*Anthocyanin coloration of flesh.*—Weak.

*Berry flesh color.*—Greyed green 192A.

*Firmness of flesh.*—Moderately firm.

*Particular flavor.*—None.

*Formation of seeds.*—Rudimentary.

*Market use of observed plant.*—Fresh market.

*Berries per bunch.*—90-120.

Pedicel:

*Length.*—0.7".

*Diameter.*—0.08".

*Color.*—Green 138B.

Woody shoot:

*Main color.*—Orange brown (grayed orange 164 B).

Age and growing conditions: Six years growing under Y system in South Joaquin Valley (hot, dry summers).

Shipping characteristics: (E.g. number of days fruit has been stored under specific conditions): Fruit was in cold storage. Stored in polyethylene bags inside Styrofoam boxes with sulfur pads. After 30 Days: rachises were 50% green; 2% berry shattering; no berry wrinkling or cracks were apparent.

DNA profile: To further the characterize the new ARRA variety DNA was extracted from dried leaf samples and DNA profiles were obtained at California Seed & Plant Lab, California USA using base pairs for 8 standard microsatellite DNA markers. The data is presented hereafter.

TABLE 2

DNA profile for 'ARRATWENTYFOUR':

| Microsatellite DNA Marker | Allele Sizes in Base Pairs | |
|---|---|---|
| M1 | 226 | 232 |
| M2 | 249 | 249 |
| M3 | 179 | 179 |
| M4 | 212 | 216 |
| M5 | 273 | 273 |
| M6 | 135 | 149 |
| M7 | 187 | 187 |
| M8 | 255 | 255 |
| M9 | 211 | 214 |
| M10 | 247 | 271 |

The ARRATWENTYFOUR variety has not been observed under all possible environmental conditions to date. Accordingly, it is possible that the phenotypic expression may vary somewhat with changes in light intensity and duration, cultural practices, and other environmental conditions.

Resistance or susceptibility to specific plant and fruit diseases and pests have not been observed to date. The plant hardiness zone and heat/cold resistance are not known.

The ARRATWENTYFOUR variety is relative productive, producing 32 bunches per vine, at a total of 58 lbs. of fruit per vine.

What is claimed is:

1. A new and distinct grapevine, botanically known as *Vitis vinifera*, identified as 'ARRATWENTYFOUR', substantially as shown and described herein.

* * * * *

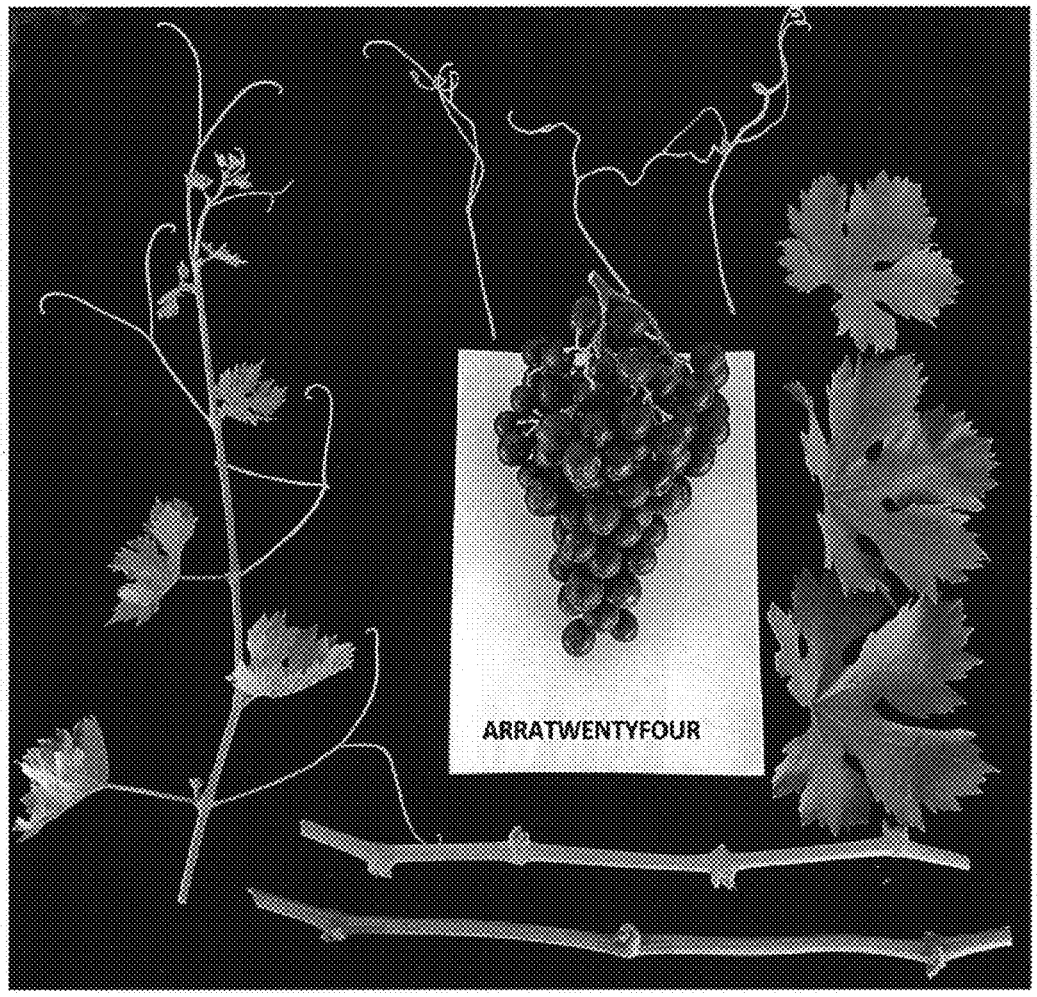
ARRATWENTYFOUR